United States Patent [19]

Hauenstein

[11] Patent Number: Plant 6,588

[45] Date of Patent: Feb. 7, 1989

[54] APPLE TREE NAMED RAFZUBIN

[75] Inventor: Walter Hauenstein, Rafz, Switzerland

[73] Assignee: Hauenstein A.G., Rafz, Switzerland

[21] Appl. No.: 61,671

[22] Filed: Jun. 15, 1987

[51] Int. Cl.[4] ..... A01H 5/03

[52] U.S. Cl. ..... Plt./34

[58] Field of Search ..... Plt./34

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A new and distinct apple tree named Rafzubin characterized by its excellent flavor, high content of sugar and acidity, long and slender stalks, form and wood similar to Golden Delicious, and lamina generally similar to Golden Delicious but biserrate, small fruit during first two years of production but normal size third year of production and thereafter, and by its excellent keeping quality.

2 Drawing Sheets

The present invention comprises a new and distinct cultivar of apple tree, botanically known as *Malus mill,* and hereinafter referred to by the cultivar name Rafzubin.

Rafzubin is a product of a planned breeding program which had the objective of creating a new variety of apple tree bearing fruit flavored like Golden Delicious, or better, and without production and storage disadvantages present in such cultivars as Cox's Orange.

Rafzubin was originated from a hybridization made in a controlled breeding program in Rafz, Canton Zurich, Switzerland in 1966. The female parent was Golden Delicious. The male parent of Rafzubin, to applicant's best knowledge, was the cultivar Cox's Orange.

Rafzubin was discovered and selected as one tree from the progeny of the stated cross by applicant in 1966 in a controlled orchard environment in Rafz, Switzerland.

The first act of asexual reproduction of Rafzubin was accomplished when grafts from scion wood were made by applicant from the initial selection in 1972 in applicant's orchard in Rafz, Switzerland. Horticultural examination of selected units initiated in 1976 has demonstrated that the combination of characteristics as herein disclosed for Rafzubin are firmly fixed and are retained through successive generations of asexual reproduction. The following observations, measurements, and comparisons describe trees grown in Rafz, Switzerland.

The following traits have been repeatedly observed and are determined to be basic characteristics of Rafzubin which in combination distinguish this apple tree as a new and distinct cultivar.

1. Excellent flavor, better than the paternal parent Cox's Orange.
2. Very high content of sugar and acidity.
3. Extremely long and slender stalk.
4. Lamina like Golden Delicious but biserrate.
5. Form and wood of tree similar to Golden Delicious.
6. Small fruit in the first two years of production, normal size from third year of production.
7. Excellent keeping quality.

Of the many commercial apple trees known to the applicant, the most similar in comparison to Rafzubin is Golden Delicious. In comparison to Golden Delicious, Rafzubin has a fruit that looks and is similar to Cox's Orange. The tree characteristics of Rafzubin are similar to Golden Delicious, except the leaves of Rafzubin are biserrate.

The accompanying color photographic drawings show typical characteristics of Rafzubin, with colors being as true as possible with illustrations of this type.

Sheet 1 illustrates several mature apples hanging from the tree.

Sheet 2 shows several apples of the new cultivar, with one being sliced open to expose the flesh and core.

In the following description, color references are made to The Royal Horticultural Society Colour Chart. The color values were determined at approximately 1:00 p.m. on Oct. 1, 1985 under sunny natural conditions at Rafz, Switzerland.

TREE

Origin: Free pollination.
Parentage:
*Seed parent.*—Golden Delicious.
*Pollen parent.*—Cox's Orange.
Classification:
*Botanic.*—*Malus mill.*
*Commercial.*—Apple.
Trunk: Similar to Golden Delicious.
Branches: Similar to Golden Delicious.
Height: Slightly smaller than Golden Delicious.
Growth habit: Similar to Golden Delicious; medium vigor and spreading habit dormant, one year old shoots are of medium thickness, have a long internode length, and numerous large lenticels.
Fruit bearing habit: Similar to Golden Delicious.
Foliage:
*Size of leaf.*—Medium.
*Shape of leaf.*—Cupped upwardly.
*Margin.*—Biserrate.
*Texture.*—Glossy.
*Color.*—Deep green, 132A.
*Petiole.*—Length medium.

FLOWERS

Form: Moderately cupped.
Size: Large.
Date of first bloom: Medium (like Cox's Orange).
Date of full bloom: Medium.
Color: Unopened, 60A.
Fruit (mature):

*Date of maturity.*—First half of October.
*Shape.*—Round-conical; more broad than long.
*Hardness.*—Medium.
*Cavity.*—Depth of stalk cavity; medium.
*Stalks.*—Very slender and extending well above cavity; very long.
*Markings.*—Green-yellow base color of skin is streaked with orange to red overcolor dominant overcolor 34A.
*Skin.*—Smooth, medium in thickness and shininess, and medium in toughness.
*Keeping quality.*—Excellent; will store at 2°-4° C. from harvest until February.
*Bruise resistance.*—Very good.

Flesh:
*Color.*—Yellow.
*Texture.*—Fine.
*Flavor.*—Sugar and acidity very well balanced.
*Juiciness.*—Medium.

*Quality.*—Excellent.

Core:
*Sessile.*—Medium.
*Bundles.*—Medium.
*Shape.*—Generally round, average in size and positioned near stalk.

Insect and disease resistance: Similar to Golden Delicious.

Primary use: Both local market and culinary.

I claim:

1. A new and distinct apple tree named Rafzubin, as described and illustrated, and particularly characterized by its excellent flavor, high content of sugar and acidity, long and slender stalks, form and wood similar to Golden Delicious, and lamina generally similar to Golden Delicious but biserrate, small fruit during first two years of production but normal size third year of production and thereafter, and by its excellent keeping quality.

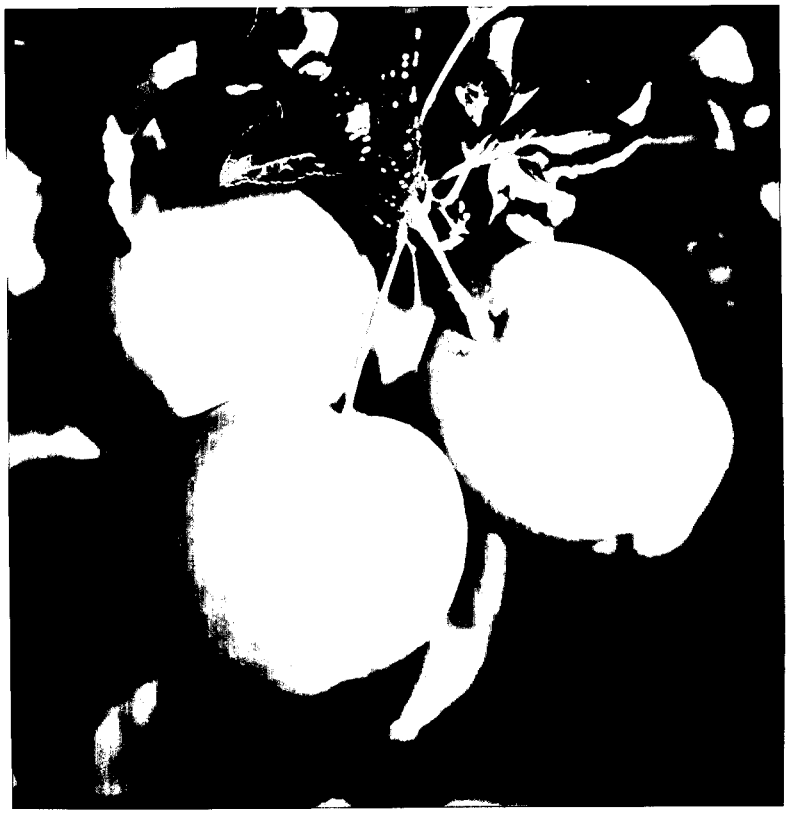

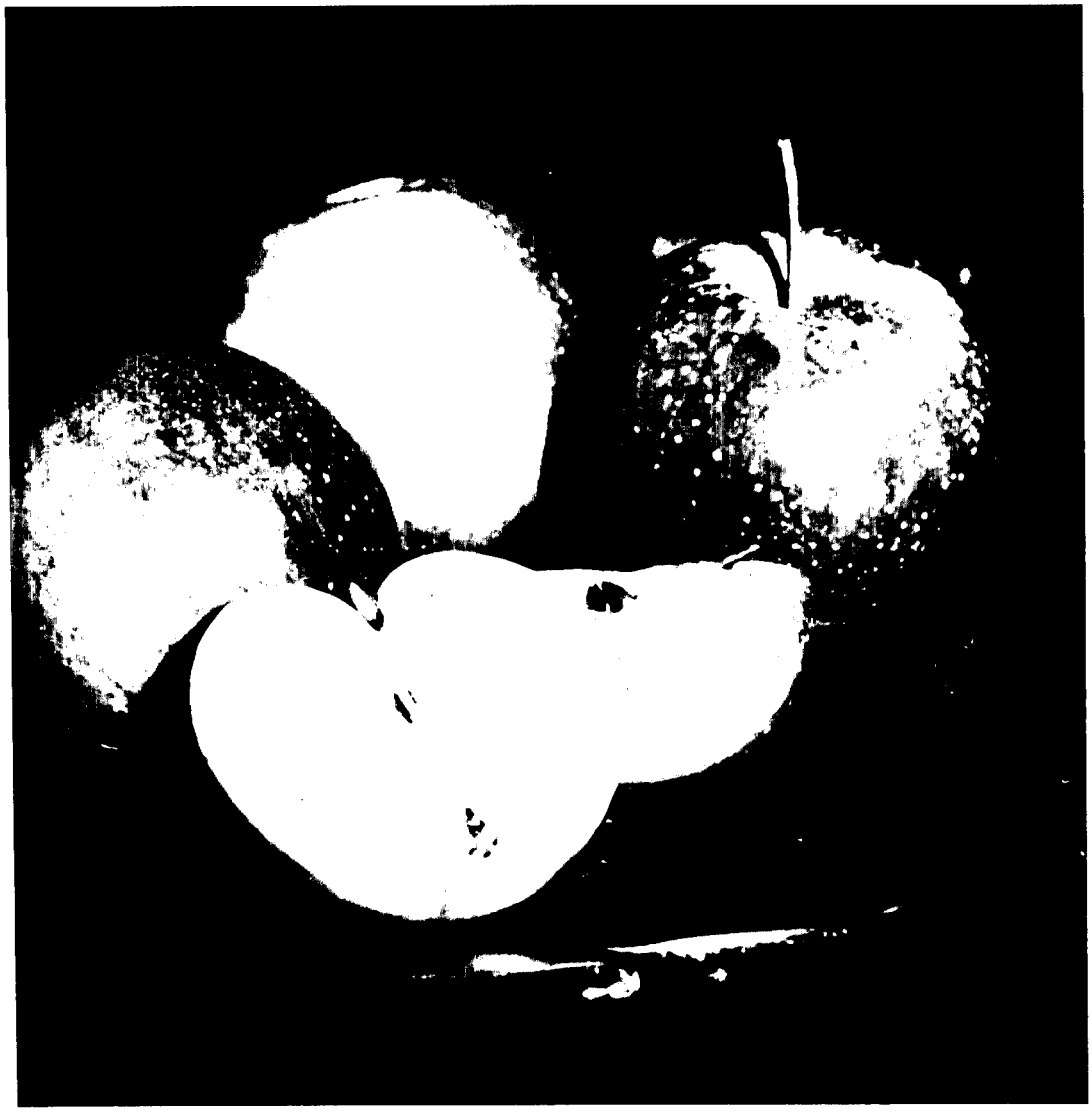

* * * * *